United States Patent [19]

Norton et al.

[11] 4,166,113

[45] Aug. 28, 1979

[54] CARDIOTONIC AGENT

[75] Inventors: Ted R. Norton; Shoji Shibata; Midori Kashiwagi, all of Honolulu, Hi.

[73] Assignee: University of Hawaii, Honolulu, Hi.

[21] Appl. No.: 902,323

[22] Filed: May 3, 1978

Related U.S. Application Data

[63] Continuation-in-part of Ser. No. 828,713, Aug. 29, 1977, abandoned.

[51] Int. Cl.$^2$ .................... A61K 37/00; C07G 7/00; A61K 35/12; A61K 35/56
[52] U.S. Cl. .................... 424/177; 260/112 R; 424/95
[58] Field of Search ............... 260/112 R; 424/177, 424/95

[56] References Cited

U.S. PATENT DOCUMENTS

| | | | |
|---|---|---|---|
| 3,951,939 | 4/1976 | Fritz et al. | 260/112.5 R |
| 4,059,694 | 11/1977 | Norton et al. | 260/112.5 R |

FOREIGN PATENT DOCUMENTS 1411184  1/1973  United Kingdom ................... 424/177

OTHER PUBLICATIONS

T. R. Norton et al., J. Pharm. Sci. 65, 1368–1374, 1976.
G. Wunderer et al., Hoppe–Seyler's Z. Physiol. Chem., 357, 239–240, 1976.
Beress et al., Hoppe–Seyler's Z. Physiol. Chem., 357, 409–414, 1976.
Shibata et al., The Pharmacologists 17(2), 218, 1975.
L. Beress et al., Toxicon 13, 359–367, (1975).
L. Beress et al., Febs. Letters 50, 311–314, (1975).
Eur. J. Biochem. 68, 193–198, (1976).
J. Pharm. Sci. 63, 1332, (1974).
Biochemistry 16, (2), (1977), 204–208.
Pharmacology 295, 55–62, (1976).

*Primary Examiner*—Delbert R. Phillips
*Attorney, Agent, or Firm*—Walter Patton; Harry E. Westlake, Jr.

[57] ABSTRACT

A novel peptide designated anthopleurin-B, hereinafter also referred to as AP-B, obtained from the sea anemone *Anthopleura xanthogrammica* is found to possess cardiotonic activity.

4 Claims, No Drawings

CARDIOTONIC AGENT

The invention described herein was made in the course of work under the Grant No. HL-15991-01 to 06 from the National Heart, Lung, and Blood Institute.

CROSS REFERENCE TO RELATED APPLICATIONS

This is a continuation-in-part application of co-pending application 828,713, filed Aug. 29, 1977, now abandoned.

BACKGROUND OF THE INVENTION

The utility of the agents, currently used to stimulate the failing heart is limited by their toxic effects on the heart or by deleterious side effects on the peripheral circulation. For example, although the cardiac glycosides are myocardial stimulants and can restore the failing heart, they do so at doses very close to those which produce toxic symptoms of cardiac arrhythmia, nausea and vomiting. Furthermore, the cardiac glycosides are ineffective under stressful conditions. The use of sympathomimetic agents are limited by associated arrhythmia, tachycardia, tachyphylaxis or altered peripheral resistance.

The compound of this invention primarily affects the contractile force of the heart muscle. This specific positive inotropic property of AP-B and the accompanying increase in cardiac output make it useful in the treatment of congestive cardiac failure or cardiac arrhythmias.

SUMMARY OF THE INVENTION

A novel peptide extracted from the sea anemone *Anthopleura xanthogrammica* has been discovered to have marked cardiac stimulant effects. Thus, it is the object of this invention to describe this novel peptide. It is a further object of this invention to describe the method of obtaining said novel peptide from sea anemone. A still further object is to describe compositions and the methods of treatment of heart failure or cardiac arrhythmias utilizing said peptide. Further objects will become apparent upon reading the following description and claims.

DESCRIPTION OF THE INVENTION

The novel peptide of the present invention, anthopleurin-B (AP-B), is obtained from the sea anemone *Anthopleura xanthogrammica* collected from Bodega Bay, California.

The sea anemones are homogenized and extracted with water or with a solution of water and a water miscible organic solvent. The crude extract, containing anthopleurin-B, is subjected to gel filtration to give a forty-fold increase in purity of anthopleurin-B. Alternatively, semipermeable membranes may be used to accomplish the results obtained by gel filtration. Cation exchange chromatography provides an excellent separation of anthopleurin-B in a purity of about 30–40% depending on the particular collection of anemones. The balance is biologically inactive peptides and the buffer salts. To obtain analytically pure salt-free material the above material is further purified by gel filtration, cation-exchange chromatography and gel adsorption chromatography. All the separation procedures in the present invention are monitored by bioassay using the isolated rat atria for determination of positive inotropic effect using the procedure described in the section headed *Bioassay*.

A preferred process for obtaining anthopleurin-B is by extracting the collected wet sea anemone *Anthopleura xanthogrammica* with water, alcohol or an aqueous-alcoholic mixture and subjecting the crude extract to gel filtration chromatography on a column packed with cross-linked dextran eluted with aqueous $NH_4HCO_3$ solution or other volatile salt solution. The active fraction is lyophilized and chromatographed on a column packed with a cation-exchange resin and eluted with a buffer or with a buffer and a gradient of an ionizable salt solution. A suitable solution for eluting the cation-exchange resin is phosphate buffer or phosphate buffer with a gradient of NaCl solution. The active fraction is lyophilized to obtain the purified anthopleurin-B. The lyophilized material is about 0.1% anthopleurin-B, the balance being about 0.2% inactive polypeptides, buffer salts and the ionizable salts. To obtain salt-free material, the dried material is chromatographed on a column packed with cross-linked dextran eluted with a salt solution to remove phosphate. The active fraction is collected and desalted by chromatography on a column packed with cross-linked dextran resin eluted with a dilute solution of a low molecular weight organic acid, such as acetic acid.

To obtain analytically pure AP-B, the desalted material is subjected to ion exchange chromatography on a column packed with sulfoethyl cellulose eluted with pyridine acetate buffers and gel adsorption chromatography on a column packed with cross-linked dextran eluted with water and ammonium acetate buffer.

In a further preferred process for obtaining anthopleurin-B from *Anthopleura xanthogrammica*, the wet anemones are cut into pieces about 2 cm. in size, homogenized and extracted with 30% aqueous ethanol. The crude extract is concentrated to an aqueous solution, which is centrifuged to remove solids and partitioned with chloroform. The chloroform extracted aqueous solution is lyophilized and the residue subjected to gel filtration chromatography on a column packed with cross-linked dextran such as Sephadex G-50, having an exclusion limit of 30,000 for globular proteins (manufactured by Pharmacia Fine Chemicals, Box 175, S-751 04, Uppsala 1, Sweden), and eluted with 0.1 M $NH_4HCO_3$. The fraction having Ve/Vo 1.84 to 2.57 contains anthopleurin-B purified forty-fold. The fraction Ve/Vo 1.84 to 2.57 is lyophilized and further purified by chromatography on a column packed with a weakly acidic cation exchange resin, such as CM-Sephadex C-25, eluted with a 0.03 M, pH 7.5 phosphate buffer with gradient elution up to 0.5 N NaCl. Anthopleurin-B elutes at Ve/Vo 6.3 to 7.0 and is lyophilized. The Ve/Vo 6.3 to 7.0 fraction is rechromatographed on a column packed with Sephadex G-50, having an exclusion limit of 30,000, and eluted with 0.03 M NaCl solution. The fraction eluted at Ve/Vo 1.75 to 2.60 is lyophilized to obtain anthopleurin-B substantially phosphate-free. The sodium chloride is removed by placing a sample on a column packed with a cross-linked dextran resin such as Sephadex G-10 having an exclusion limit of 700 followed by approximately three times sample volume of 20% sodium chloride solution and eluted with 0.017 M acetic acid. Salt-free anthopleurin-B of 30 to 40% purity elutes at Ve/Vo 0.88 to 1.25. Since associated polypeptides were found to be inactive, this material is adequate for pharmacological studies.

To obtain AP-B free of associated inactive peptides, the Ve/Vo 0.88 to 1.25 fraction is dissolved in distilled water and chromatographed on Cellex-SE cellulose (Bio.Rad Laboratories, Richmond, California), equilibrated with 0.05 M pyridine in 25% acetic acid. AP-B is eluted by a linear gradient of equal volumes each of 0.05 M pyridinium acetate pH 2.7 and 1.0 M pyridinium acetate at Ve/Vo=1.85-2.19.

This fraction is lyophilized and then dissolved in distilled water. The solution is chromatographed on Sephadex G-25, fine, and eluted with 6% nbutanol gradient with 0.05 M NH₄OAc (pH 6.0) also in 6% n-butanol. The AP-B is eluted at about Ve/Vo=2.8. This material now is analytically pure as judged by amino acid analysis.

The preferred process for obtaining pure anthopleurin-B is illustrated by the following Scheme 1.

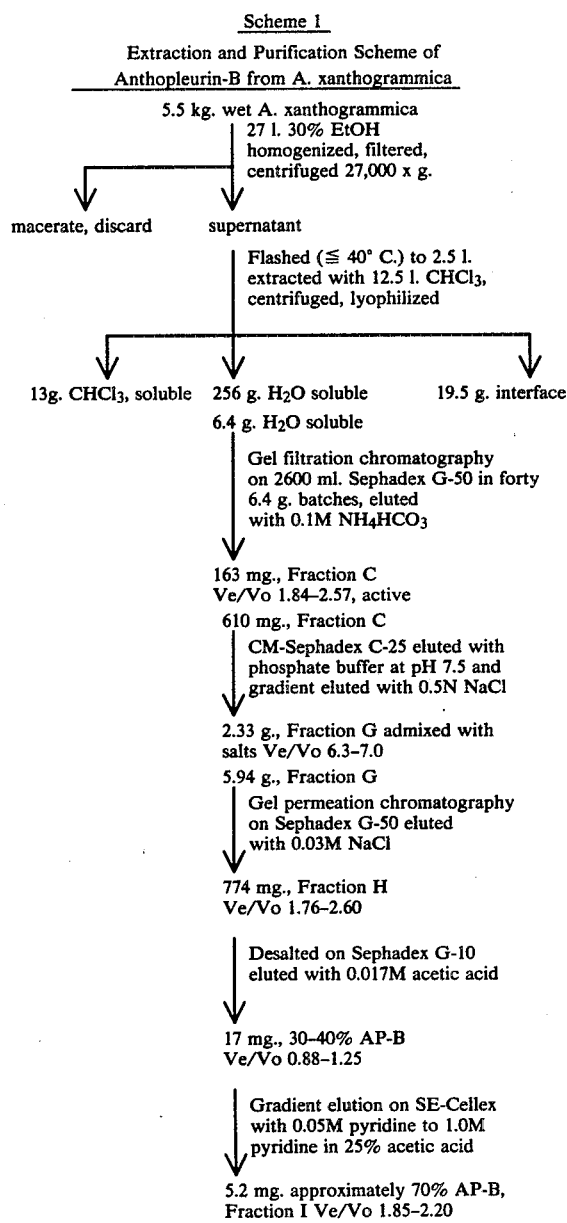

Scheme 1
Extraction and Purification Scheme of Anthopleurin-B from A. xanthogrammica 5.5 kg. wet A. xanthogrammica
  27 l. 30% EtOH homogenized, filtered, centrifuged 27,000 × g.

macerate, discard    supernatant
  Flashed (≦ 40° C.) to 2.5 l. extracted with 12.5 l. CHCl₃, centrifuged, lyophilized 13g. CHCl₃ soluble    256 g. H₂O soluble    19.5 g. interface
6.4 g. H₂O soluble
  Gel filtration chromatography on 2600 ml. Sephadex G-50 in forty 6.4 g. batches, eluted with 0.1M NH₄HCO₃

163 mg., Fraction C Ve/Vo 1.84-2.57, active 610 mg., Fraction C
  CM-Sephadex C-25 eluted with phosphate buffer at pH 7.5 and gradient eluted with 0.5N NaCl 2.33 g., Fraction G admixed with salts Ve/Vo 6.3-7.0

5.94 g., Fraction G
  Gel permeation chromatography on Sephadex G-50 eluted with 0.03M NaCl 774 mg., Fraction H Ve/Vo 1.76-2.60

Desalted on Sephadex G-10 eluted with 0.017M acetic acid 17 mg., 30-40% AP-B Ve/Vo 0.88-1.25

Gradient elution on SE-Cellex with 0.05M pyridine to 1.0M pyridine in 25% acetic acid 5.2 mg. approximately 70% AP-B, Fraction I Ve/Vo 1.85-2.20

-continued
16.4 mg., Fraction I
  Gradient eluted on Sephadex G-25 with 6% n-butanol to 0.05M NH₄OAc 11.4 mg. Approximately 80% pure AP-B Ve/Vo 2.5-3.15

The novel peptide, AP-B, of the present invention is administered to the patient with heart failure or cardiac arrhythmias at a rate of from about 0.01 to about 5 μg./kg. of body weight per hour either by infusion or by a single dose as determined by those skilled in the art.

For such usage the compound of this invention may be administered orally or parenterally as such or admixed with conventional pharmaceutical carriers. The parenteral route is preferred. It may be administered orally in such forms as tablets, dispersible powders, granules, capsules, syrups and elixirs, and parenterally as solutions, suspensions, dispersions, emulsions, and the like, e.g., a sterile injectable aqueous solution. The compound may also be altered chemically such as by acylation and esterification, or physically such as preparing an artificial liposome to reduce peptic destruction. The preferred route of administration is by injection.

A preferred pharmaceutical composition of AP-B comprises the active ingredient in gelatin and phenol preservative. A further preferred pharmaceutical composition for injection comprises sterile powdered lyophilized AP-B which in the dry form is stable at room temperature. The lyophilized powder may be packaged in vials containing hydrolyzed gelatin. AP-B may be reconstituted at the time of use by dissolving in a convenient volume of sterile water or sodium chloride solution for injection in such a manner that the individual dose will be contained in 1-2 ml. of solution. The reconstituted solution should be refrigerated and used before decomposition or preferably within 24 hours.

These pharmaceutical preparations may contain up to about 90% of the active ingredient in combination with the carrier or adjuvant.

The cardiotonic effective dosage of active ingredient employed for the treatment of congestive heart failure or cardiac arrhythmias may vary depending on the severity of the condition being treated. However, in general, satisfactory results are obtained with anthopleurin-B is administered at an hourly dosage of from about 0.01 μg. to about 5 μg./kg. of animal body weight, or in sustained release form for the period of time which is determined by those skilled in the art.

Dosage forms suitable for internal use comprise from about 2 to about 360 μg. of the active compound in intimate admixture with a solid or liquid pharmaceutically acceptable carrier or diluent. The preferred pharmaceutical compositions from the standpoint of preparation and ease of administration are injectable compositions, particularly those containing about 0.05 μg. to about 10 μg./ml.

Bioassay for Determining Positive Inotropic Effect

Bioassays of the solutions containing anthopleurin-B are performed on isolated atria of rat hearts. The atrium is separated from the rest of the heart and suspended in an isolated organ bath (20, 25, or 50 ml.) containing Krebs Ringer bicarbonate medium (pH 7.4) of the following composition in distilled deionized water (in mmoles): $Na^+$, 145; $K^+$, 6.02; $Ca^{+2}$, 1.22; $Mg^{+2}$, 1.33;

Cl$^-$, 126; HCO$_3^-$, 25.3; PO$_4^{-3}$, 1.2; SO$_4^{-2}$, 1.33; and glucose, 5.5. The temperature of the organ bath is maintained at 30° C., and the Krebs-Ringer medium is continuously aerated with 95% O$_2$-5% CO$_2$.

The spontaneously beating atrial preparation is connected by a thin silk thread to a force-displacement transducer (Grass Model FT.03), and the contractile movements are recorded on a six-channel polygraph Grass Model 7. The preparation is allowed to equilibrate under 750 mg. tension for 60 minutes prior to beginning an assay. After this equilibration, during which the preparations are washed out every 30 minutes, the spontaneous beat rate of the atria remains constant; the change during a 10-minute observation being less than 5 beats/min. The changes in contractile force and rate produced by the test solution containing anthopleurin-B is expressed as a percentage increase or decrease in tension and rhythm, with the period immediately preceding addition of test solution to the tissue bath as the baseline for comparison.

PHYSICAL AND CHEMICAL PROPERTIES OF AP-B

For the purpose of obtaining electrophoretic and amino acid analysis the anthopleurin-B obtained in Example 1, below, was rechromatographed on CM Sephadex C-25, Sephadex G-50 and G-10 according to the process set forth in Example 1, Steps c, d and e, respectively. The doubly purified material was subject to electrophoretic analysis using commercially available pre-cast 12% acrylamide gels and matched buffer systems obtained from Bio.Rad Laboratories, 32nd and Griffin, Richmond, California.

Isoelectric focusing gave the isoelectric point at a pH=9.05. Disc gel electrophoresis with 12% polyacrylamide gel at pH 3.6 gave an R$_f$ value of 0.64 versus methyl green tracking dye. AP-B does not enter a basic gel at pH 8.9 indicating possible lack of available carboxyls. Sodium dodecyl sulfate (SDS) disc gel electrophoresis using a 10% gel indicated a m.w. of about 5,200 after incubation with dithioerythritol, using RNase A and pancreatic trypsin inhibitor (PTI) for comparison. The molecular weight is so low that these values are only approximate. AP-B was determined to be a peptide on the basis of loss of biological activity after treatment with proteolytic enzymes. Acid hydrolysis indicated the approximate following amino acid composition: (Asp or Asn)$_5$, Thr$_1$Ser$_4$, (Glu or Gln)$_1$, Pro$_5$, Gly$_7$, Ala$_2$, (Cys/2)$_6$Val$_1$, Ile$_2$, Leu$_2$, Tyr$_1$, Phe$_1$, Lys$_3$, His$_2$, Arg$_2$, Trp$_2$.

It is believed that the partial amino acid sequence starting with the N-terminal end is as follows:
Gly-Val-Pro-Cys-Leu-Cys-Asp-Ser-Asp-Gly-Pro-Pro-Asn-Arg-Gly-Asn-Thr-Leu-Ser-Gly-Ile-Leu-Trp-Phe--Ala-Pro-Ser-Gly-(---)-Pro-(---)-Gly-Trp-(---) wherein (---) designates undetermined amino acid(s).

The abbreviated designations, which are used herein for the amino acid components are as follows:

| Abbreviated Designation | Amino Acid |
| --- | --- |
| Lys | lysine |
| His | histidine |
| Arg | arginine |
| Asp | aspartic acid |
| Thr | threonine |
| Ser | serine |
| Gln | glutamine |

-continued

| Abbreviated Designation | Amino Acid |
| --- | --- |
| Pro | proline |
| Gly | glycine |
| Ala | alanine |
| Cys/2 | cysteine |
| Val | valine |
| Ile | isoleucine |
| Leu | leucine |
| Tyr | tyrosine |
| Trp | tryptophan |
| Asn | asparagine |
| Glu | glutamic acid |
| Phe | phenylalanine |

Anthopleurin-B is relatively stable at neutral and lower pH values and is very soluble in deionized water.

Anthopleurin-B can be further characterized by its pharmacological characteristics. The pharmacological characteristics indicate anthopleurin-B is about 200-1000x as potent as ouabain in positive inotropic effect, having an ED$_{50}$ at 1.5-3.0×10$^{-9}$ M on isolated rat atria. It does not show any chronotropic effect.

EXAMPLE 1

Isolation of Anthopleurin-B from *Anthopleura xanthogrammica*

Step a—Extraction

*Anthopleura xanthogrammica* (Brandt) specimens were collected, preserved in 95% ethanol and stored at 4° C. prior to extraction. Wet, drained anemones (5.5 kg.) were cut into <2 cm. pieces and homogenized batchwise in a blender for five minutes with 27 liters of 30% ethanol. This volume of ethanol includes the ethanol used to preserve the specimens. The mixture was allowed to stand for one week at 20° C. with occasional stirring, and then filtered through six layers of cheesecloth. The filtrate was flash evaporated at ≦40° C. to about 2.5 liters and partitioned with 12.5 liters of chloroform batchwise, by thorough agitation followed by centrifugation at 27,000×g. for 30 minutes. This produced 13 g. of chloroform solubles, 19.5 g. of interface solids, and 256 g. (lyophilized weight) of water solubles containing anthopleurin-B.

Step b—Gel Permeation Chromatography

The 256 g. of crude water soluble extract, containing anthopleurin-B, was split into forty equal portions for chromatographic separation on Sephadex G-50 having an exclusion limit 30,000 (obtained from Pharmacia Fine Chemicals). A column 53×8.3 cm. containing 2,600 ml. of wet Sephadex G-50 (Vo=825 ml.) was equilibrated with 0.1 M NH$_4$HCO$_3$ saturated with chloroform (to prevent microorganism growth). Fifty ml. of water containing 6.4 g. of crude water soluble extract containing anthopleurin-B was placed on the column and eluted with 0.1 M NH$_4$HCO$_3$ at 8-9 ml./min. at room temperature.

The bioassays for contractile force of the isolated rat atria were carried out as described in the section headed *Bioassay*. The results showed fraction C contained ca. 99% of the cardiotonic activity. A total of 6.4 g. of fraction C was thusly produced from 256 g. of crude water solubles obtained in Step a.

Step c—Ion-exchange Chromatography

A 610 mg. portion of fraction C, obtained in Step b, was dissolved in 5 ml. of 0.03 M $Na_x(PO_4)_y$ buffer at pH 7.5 and put on a 48×4 cm. column (Vo=205 ml.) containing 600 ml. of wet cation exchange resin CM-Sephadex C-25 (obtained from Pharmacia Fine Chemicals) equilibrated with the same buffer saturated with chloroform. A stirred reservoir of 1,500 ml. of the buffer was connected to the column and after 110 ml. of buffer had flowed through the column, the reservoir volume was maintained constant by feeding with a 0.03 M $Na_x(PO_4)_y$ buffer 0.5 M in NaCl adjusted to pH 7.5 for gradient elution. Both solutions were saturated with chloroform. The flow rate of about 3 ml./min. was maintained and the run was made at room temperature. The effluent was monitored using U.V. absorbance at 280 nm with a Model UA-5 Absorbance Monitor, obtained from Instrument Specialties Company, P.O. Box 5247, 4700 Superior Street, Lincoln, Nebraska 68505. The fraction having the Ve/Vo range between 6.3 and 7.0 and centered at Ve/Vo 6.60 was designated fraction G and found to be active according to the bioassay set forth under the heading *Bioassay*. Fraction G was lyophilized to give 2.33 g. of material, containing anthopleurin-B admixed with salts.

Anthopleurin-B showed no signs of deterioration when kept at −20° C. for a year as lyophilized fraction C, obtained in Step b, or as lyophilized fraction G.

Step d—Purification for Analysis

Fraction G, obtained in Step c, was further purified by gel filtration chromatography on Sephadex G-50 having an exclusion limit 30,000 (obtained from Pharmacia Fine Chemicals). An 8.3×51 cm. column (Vo=790 ml.) containing 2450 ml. of wet G-50 was equilibrated with 0.03 M NaCl solution saturated with chloroform. A solution of 5.94 g. fraction G dissolved in 35 ml. $H_2O$ was put on the column and eluted at room temperature with the equilibrating solution. Fraction H was collected at Ve/Vo 1.76–2.60 centered at Ve/Vo 2.27. No U.V. absorbing material at 280 nm appeared before fraction H and only a trace appeared thereafter. Fraction H was lyophilized to give 774 mg. of anthopleurin-B (including the NaCl).

Step e—Desalting

The salt was removed by using a column packed with Sephadex G-10 having an exclusion limit of 700 (obtained from Pharmacia Fine Chemicals). The 774 mg. of fraction H, obtained in Step d, was dissolved in 10 ml. of water and put on a 31×3.1 cm. column packed ith 230 ml. wet Sephadex G-10 equilibrated with 0.017 M acetic acid saturated with chloroform. The sample was followed by 5.0 ml. of 20% NaCl and then the equilibrating solution. Anthopleurin-B emerged completely and sharply at void volume (Ve/Vo 0.88–1.25) and was salt free. It was immediately lyophilized to give 17 mg. of 30–40% pure anthopleurin-B.

Step f—Gradient Elution on SE Cellulose

The peptide (17.0 mg.) obtained by the process set forth in Steps (a) to (e), was dissolved in 0.5 ml. of distilled water and placed on a 2.1×39 cm. column packed with 135 ml. wet Cellex-SE cellulose (Bio.Rad Laboratories, Richmond, California), equilibrated with 0.05 M pyridine in 25% acetic acid. Using a 250 ml. stirred reservoir of the 0.05 M pyridine, a gradient with 1.0 M pyridine in 25% acetic acid was produced by allowing the latter to flow into the former as it was used in elution. The active peptide was eluted at Ve/Vo 1.85–2.2 and after lyophilization weighed 9.2 mg.

Step g—Gradient Elution on Sephadex G-25

A 16.4 mg. sample of peptide produced as in Step (f) was dissolved in 0.8 ml. distilled water and placed on a 1.1×58 cm. column packed with 55 ml. Sephadex G-25, fine, equilibrated with 6% 1-butanol in distilled water. Using a 500 ml. stirred reservoir of the 6% butanol a gradient with 0.05 M $NH_4OAc$ in 6% butanol was produced by allowing the latter to flow into the former as it was used for elution. The active peptide was eluted at Ve/Vo 2.5–3.15 and after lyophilization gave 11.4 mg. of about 80% pure anthopleurin-B.

EXAMPLE 2

Sterile Suspension of AP-B for Injection

The anthopleurin-B obtained in Example 1 is mixed with sterile hydrolyzed gelatin to the extent of 3.5 μg. anthopleurin-B to about 10 mg. hydrolyzed gelatin and packaged in sterile vials sealed in an atmosphere of nitrogen using conventional techniques. The AP-B is reconstituted at the time of use by the addition of 1 ml. sterile water. The injectable solution is suitable for administration once an hour for a body weight of 70 kg.

What is claimed is:

1. A peptide designated anthopleurin-B which has the following amino acid composition:

| amino acid | number of residues |
| --- | --- |
| Aspartic acid or asparagine | 5 |
| Threonine | 1 |
| Serine | 4 |
| Glutamic acid or glutamine | 1 |
| Proline | 5 |
| Glycine | 7 |
| Alanine | 2 |
| Cysteine | 6 |
| Valine | 1 |
| Isoleucine | 2 |
| Leucine | 2 |
| Tyrosine | 1 |
| Phenylalanine | 1 |
| Lysine | 3 |
| Histidine | 2 |
| Arginine | 2 |
| Tryptophan | 2 | having the following physical and chemical properties:
   (a) molecular weight of about 5,200;
   (b) an isoelectric point of about pH 9.05;
   (c) $R_f$=0.64 determined by disc gel electrophoresis with 12% polyacrylamide gel at pH 3.6, using methyl green dye as a standard prepared by
   (d) extracting sea anemone with water or with an aqueous-alcoholic mixture;
   (e) subjecting the extract to gel filtration chromatography on a column of crosslinked dextran eluted with $NH_4HCO_3$ solution and collecting and lyophilizing the active fraction;
   (f) subjecting the active fraction to chromatography on a column of cation exchange resin eluted with a phosphate buffer with a gradient of NaCl and collecting and lyophilizing the active fraction;
   (g) subjecting the active fraction obtained in (f) to chromatography on a column of cross-linked dextran eluted with a NaCl solution and collecting and lyophilizing the active fraction;

(h) desalting the active fraction obtained in (g) by chromatography on a column of crosslinked dextran eluted with dilute acetic acid and collecting and lyophilizing the active fraction.

2. The pharmaceutical preparation which comprises the peptide of claim 1 in admixture or conjunction with a pharmaceutically acceptable carrier.

3. The method of treating heart failure by administering a cardio effective amount of the peptide of claim 1.

4. The method of treating cardiac arrhythmias by administering a cardio effective amount of the peptide of claim 1.

* * * * *